United States Patent [19]

Polmanteer

[11] 4,138,382

[45] Feb. 6, 1979

[54] HYDROPHILIC, WATER-SWELLABLE, CROSSLINKED, COPOLYMER GEL AND PROSTHESIS EMPLOYING SAME

[75] Inventor: Keith E. Polmanteer, Midland, Mich.

[73] Assignee: Dow Corning Corporation, Midland, Mich.

[21] Appl. No.: 901,954

[22] Filed: May 1, 1978

[51] Int. Cl.$^2$ ............................................. C08F 220/56
[52] U.S. Cl. ....................... 260/29.6 TA; 260/29.6 H; 260/29.7 H; 526/279; 528/32; 3/36; 128/DIG. 21
[58] Field of Search ................... 260/29.6 H, 29.6 TA, 260/29.7 H; 526/279; 528/32; 3/36

[56] References Cited

U.S. PATENT DOCUMENTS

| | | | |
|---|---|---|---|
| 2,820,798 | 1/1958 | Bailey | 260/326.5 |
| 3,004,950 | 10/1961 | Tousignant | 260/46.5 |

FOREIGN PATENT DOCUMENTS

| | | |
|---|---|---|
| 714630 | 7/1965 | Canada. |
| 832505 | 1/1970 | Canada. |
| 834267 | 2/1970 | Canada. |

Primary Examiner—Paul R. Michl
Attorney, Agent, or Firm—Max J. Kenemore

[57] ABSTRACT

A hydrophilic, water-swellable, crosslinked gel is produced by copolymerizing a water soluble vinylic constituent in aqueous solution with olefinic hydrolyzable silanes which contain low molecular weight alkoxy groups. Copolymerization is via the unsaturated groups and crosslinking is by condensation reactions. The copolymer is swellable to a finite extent or to an infinite extent depending upon the water/vinylic monomer volume ratio and upon the vinylic monomer:silane mole ratio. Non-toxic embodiments of the gel are especially useful as prosthesis fillers. Such gels can be used to fill the prosthesis before implantation or the prosthesis can be swollen with an aqueous solution after implantation.

9 Claims, 5 Drawing Figures

HYDROPHILIC, WATER-SWELLABLE, CROSSLINKED, COPOLYMER GEL AND PROSTHESIS EMPLOYING SAME

BACKGROUND OF THE INVENTION

This invention relates generally to hydrophilic gels and, more specifically, to copolymers of olefinic hydrolyzable silanes and water soluble vinylic constituents in aqueous solution which polymerize through the unsaturated groups and crosslink by condensation, and to their use as prosthesis fillers.

PRIOR ART

Gels of various kinds are known for use as prosthesis fillers. Gels are chosen to give the prosthesis the proper body and resilience. Silicone gels made in accordance with U.S. Pat. No. 3,020,260 are good examples of those which are especially useful as mammary prosthesis fillers. In the past, preferred gels have been liquid methyl silicone resins, capable of being vulcanized to an elastomer state, blended with a dimethyl silicone fluid.

Such gels have many advantages for use as mammary prosthesis fills and have met with great commercial success in this field. However there are certain areas where improvement in the material is desirable.

One such area is the hydrophobic nature of the gel. Hydrophobic gels are not readily dispersed by the body if they should move across the prosthesis walls. The prosthesis walls are usually formed from a silicone rubber polymer or copolymer which has an osmotic nature. Although movement in great quantity of liquids across the prosthesis walls is not anticipated, some seepage is not surprising.

The use of a hyrophilic gel to fill mammary prostheses is desirable. However, a hydrophilic gel with suitable properties has not been readily available.

In the past, it has also been an undesirable aspect of mammary implant surgery that a relatively large incision is required for implanting the prosthesis. Efforts have been made to solve this problem. Such solutions are typified by the disclosure in U.S. Pat. No. 3,416,160 to Arion. In that disclosure an inflatable chamber (balloon) having a filler neck is inserted through a small incision. The chamber is then inflated to size through the neck.

The need for a neck-like filling mechanism in the Arion device is seen as a disadvantage typical of the prior art. A mammary prosthesis which can be implanted through a relatively small incision and subsequently expanded while avoiding the need for a filler neck is desirable.

SUMMARY OF THE INVENTION

It is therefore an object of this invention to present a hydrophilic gel.

It is also an object of this invention to furnish a hydrophilic gel which is water swellable to an infinite extent.

It is a further object of this invention to furnish a hydrophilic gel which is water swellable to a finite extent.

It is still another object of the present invention to supply a hydrophilic gel which is water swellable to an infinite extent and which is soluble in body fluid.

It is also an object of this invention to furnish an improved mammary prosthesis.

It is an object of this invention to present a mammary prosthesis which is implantable through a relatively small incision.

It is still a further object of this invention to achieve a finitely water swellable gel having improved flexural strength.

These and other objects are accomplished by the present invention, which comprises, generally speaking, a water swellable gel. The gel includes a crosslinked copolymer of a water soluble vinylic constituent in aqueous solution and an olefinic hydrolyzable silane having the formula $X_m R_n Si(OR')_{4-(n+m)}$. X is an unsaturated group, m is at least 1, R and R' are organic radicals with n being 0-2. The volume ratio of water to vinylic constituent is from about 0.5 to about 10 while the mole ratio of vinylic constituent to hydrolyzable silane is from about 50 to about 600. Polymerization in the copolymer is via the unsaturated groups, and crosslinking is by condensation reactions.

In one embodiment, the volume ratio of water to vinylic constituent and the mole ratio of vinylic constituent to hydrolyzable silane is selected so that the gel is water swellable to an infinite extent.

In another embodiment, the ratios are selected to that the gel is water swellable to a definite extent.

A surgically implantable prosthesis filled with the novel gel is included within the scope of this invention. In one embodiment the prosthesis is filled with an amount of the novel gel sufficient to give it support and shape prior to implantation. Alternatively, the prosthesis is filled with an amount of gel insufficient to completely expand and support it. Such a prosthesis is implanted through a relatively small incision. After the prosthesis is implanted, the gel can be furnished with additional water so that it swells to support the prosthesis.

Figure 1:
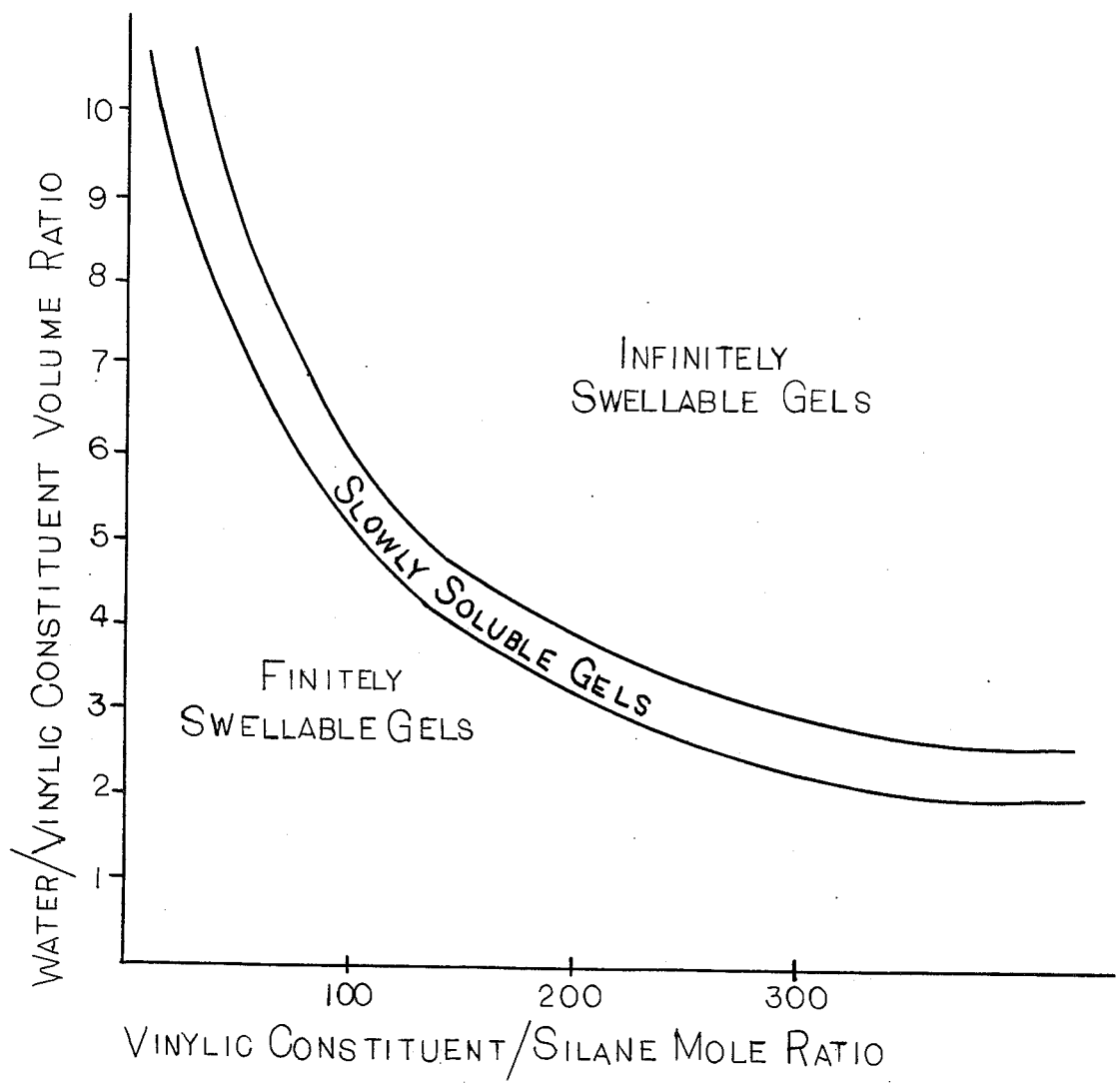
FIG. 1 is a graph which shows the swellability of gels made according to the present invention depending upon the water/vinylic constituent ratio and the vinylic constituent/silane ratio.

Referring more specifically to FIG. 1, there is shown a graph which plots the water/vinylic constituent ratio against the vinylic constituent/silane ratio. The water/vinylic constituent ratios are volume ratios and the vinylic constituent/silane ratios are mole ratios.

A combination of ratios which fall below the bottom curve on the graph give gels which are finitely swellable. That is, such gels absorb water and swell (sometimes several thousand percent in volume), but do not dissolve in water over long periods of time.

Ratio combinations above the top curve result in infinitely swellable gels. Such gels are found to be soluble in water in relatively short times.

Gels have ratios which fall between the curves on the graph are found to be slowly soluble. Although they do not dissolve in water at once, they solubilize over long periods of time.

For the purposes of the following description and claims, infinitely swellable gels are defined as those above the top curve; slowly soluble gels are defined as those between the curves and finitely soluble gels are defined as those below the bottom curve.

For example, a gel having a water/vinylic constituent volume ratio of 6 and a vinylic constituent/silane mole ratio of 200 would be defined as an infinitely swellable gel. A gel having a water/vinylic constituent volume ratio of 6 and a vinyl constituent/silane mole ratio of 100 would be defined as a slowly soluble gel; and a gel having a water/vinyl constituent volume ratio of 1.5 and a vinyl constituent/silane mole ratio of 300 would, for example, be defined as a finitely swellable gel.

Useful water/vinylic constituent ratios range from about 0.5 to about 10 while useful vinylic constituent/silane ratios range from about 50 to about 600. Higher ratios generally result in progressively more fluid gels, and lower ratios produce increasingly more solid gels.

Any suitable non-toxic water soluble vinylic constituent can be used. The term "vinylic" as employed herein is intended to mean that the constituent contains at least one unsaturated aliphatic linkage in the form of $CH_2=CR$.

N-vinylpyrroledone monomer is the preferred vinylic constituent because of the excellent results which are obtained using it and because of its long history of biocompatability. Other vinylic constituents can be used in minor amounts to make copolymers and terpolymers with N-vinylpyrroledone. Such copolymers and terpolymers can be selected to modify then properties of the gel. For example, a copolymer or terpolymer can be used to give a finitely swellable gel added flexibility and cohesiveness.

Typical such other constituents are hydroxyalkyl methacrylates of the formula

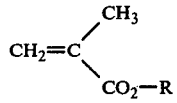

wherein R is $-CH_2CH_2OH$,

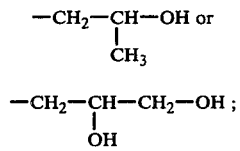

and 2,4-pentadiene-1-ol; acrylamide derivatives of the formula

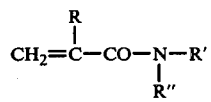

wherein R = $-H$ or $CH_3$ and R' and R'' are H, $-CH_3$, $-C_2H_5$ or $-CH_2CHOHCH_3$.

All of the above constituents have been accepted for use in medical applications and are thus suited for use as prosthesis fillers.

Silanes according to the generic formula $X_mR_nSi(OR')_{4-(n-m)}$ are useful in the present invention. Typically, X is vinyl, an allyl, a methacrylate or mixtures thereof.

R' is typically methyl or ethyl. R' can have more than 2 carbons in some cases but this is generally not preferred because higher carbon chains require a hydrolysis catalyst in order to be useful. Hydrolysis catalysts can be bases (e.g. $NH_4OH$, NaOH and KOH) or acids (e.g. mineral acids or fatty acids).

R is typically methyl or ethyl.

Good results have been observed when vinyl trimethoxy silane is selected. It is readily available and provides a maximum number of crosslinking sites. Other examples of useful silanes according to the generic formula $X_mR_nSi(OR')_{4-(n+m)}$ are vinyl triethoxy silane, ethyl vinyl dimethoxy silane, allyltrimethoxysilane and 3-trimethoxysilyl-propylmethacrylate.

The volume ratios of water to vinylic constituent and the mole ratio of vinylic constituent to silane are important in determining the degree of water swellability of the crosslinked copolymer. For certain applications it is desirable to obtain a gel having a finite swellability. Other applications lend themselves more to the use of an infinitely swellable gel. Typical applications for finitely and infinitely swellable gels are found below in the discussion of the use of the gel in mammary prostheses.

Gels according to the present invention are useful in a variety of applications. Non-toxic gels for medical uses is an illustrative application. Typical of such an application is the use of the gel as a mammary prosthesis filler as described in connection with FIGS. 2 through 5 below.

Figure 2:
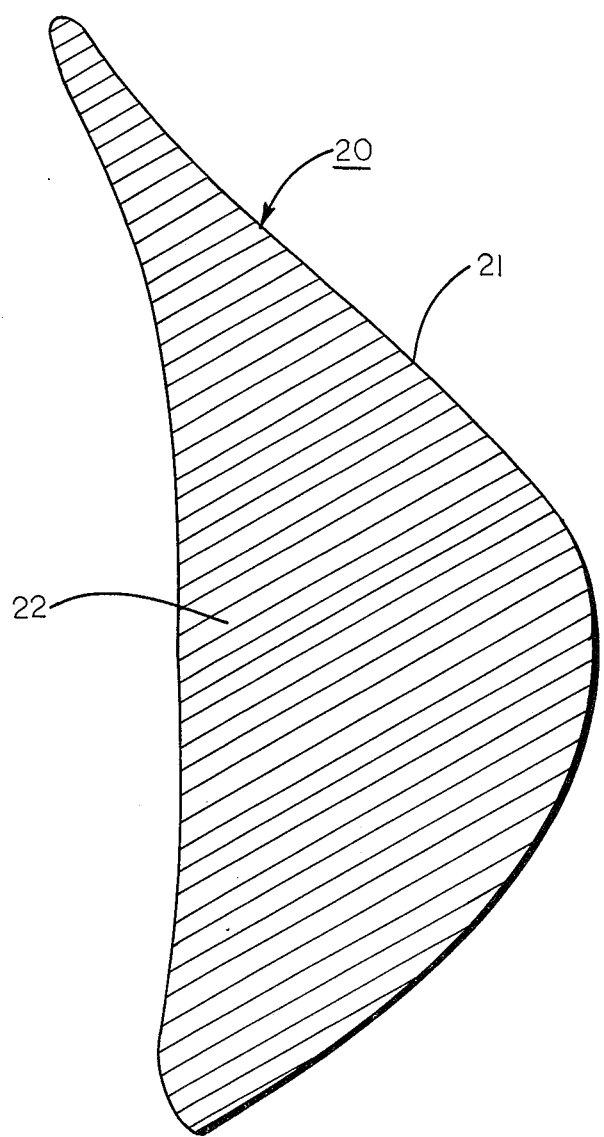
FIG. 2 shows schematically and in cross-section a mammary prosthesis filled with a water swellable gel.

Referring more specifically to FIG. 2 there is shown a mammary prosthesis 20. The prosthesis is a flexible container 21 having the general shape of a human breast and filled with a water swellable gel 22.

Container 21 is formed of a flexible silicone rubber membrane. Container 21 could be formed in several ways such as by a dip process on a mandrel, by vacuum forming or by assembly of a cup portion to a back wall utilizing vulcanization or adhesion to join the parts.

Container 21 may be formed of a physiological inert elastomeric material which includes several plastics. Silicone rubbers are preferred because of their relative strength. Under certain circumstances organic rubbers made from butyl polymer or the natural polymer from the hevea tree could be utilized. The silicone rubbers which may be used in this invention can be either of the heat vulcanizing or room temperature vulcanizing type. Since these rubbers are intended for medical purposes, fillers, vulcanizing agents and other constituents should be chosen for their non-toxic, physiological inert characteristics.

Gel 22 in this embodiment is the infinitely swellable gel of the present invention. The use of an infinitely swellable gel for the purposes of this illustration is not intended to be limiting. A finitely swellable gel could also be used.

The infinitely swellable gel, however, is preferred for this embodiment. In the unlikely event of breakage of container 21 or in the event of seepage of gel 22 through container 21 (e.g. by osmosis), the infinitely swellable hydrophilic gel is observed to be absorbed and dissipated by the body. The dissipation of the hydrophilic gel by the body represents an improvement over previously known hydrophobic gels.

Figure 3:
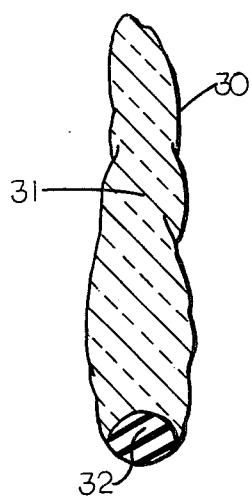
FIG. 3 shows schematically and in cross-section a mammary prosthesis partially filled with a finitely swellable gel.

Referring more specifically to FIG. 3 there is shown a mammary prosthesis 30 which contains finitely swellable gel 31. Prosthesis 30 is formed from any useful material as described in connection with container 21 of FIG. 2. Prosthesis 30 has an overall flat shape which enables it to be surgically implantable through a relatively small incision.

Self-sealing valve 32 is located at one end of the prosthesis. Valve 32 is of the type disclosed in U.S. Pat. No. 3,919,724. Such valves are generally made from a silicone gel having a higher penetrometer reading so that it will be self sealing upon penetration by a needle. The sealing gel is contained within a shell (not shown) which is adhered to the inside of prosthesis 30.

Gel 31 is contained in prosthesis 30 so that there are no significant air pockets or voids. However, gel 31 does not at this point expand prosthesis 30 to its fullest extent.

Figure 4:
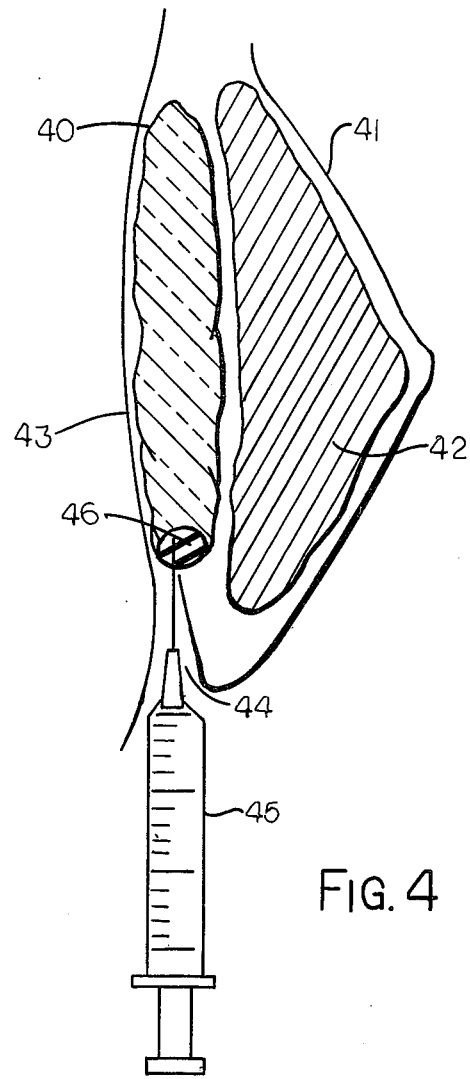
FIG. 4 shows schematically and in cross-section the prosthesis of FIG. 3 being injected with an aqueous fluid after having been surgically implanted.

Referring more specifically to FIG. 4 there is shown prosthesis 40 (which corresponds to prosthesis 30 of FIG. 3) after it has been surgically implanted. Prosthesis 40 has been implanted in breast 41 between mammary gland 42 and chest walls 43 through incision 44. Incision 44 is small relative to an incision necessary for implantation of an already expanded prosthesis, such as that shown in FIG. 2.

Hypodermic needle 45 is shown penetrating valve 46. Needle 45 is used to inject an amount of sterile water or some other sterile aqueous fluid into the finitely swellable gel.

Figure 5:
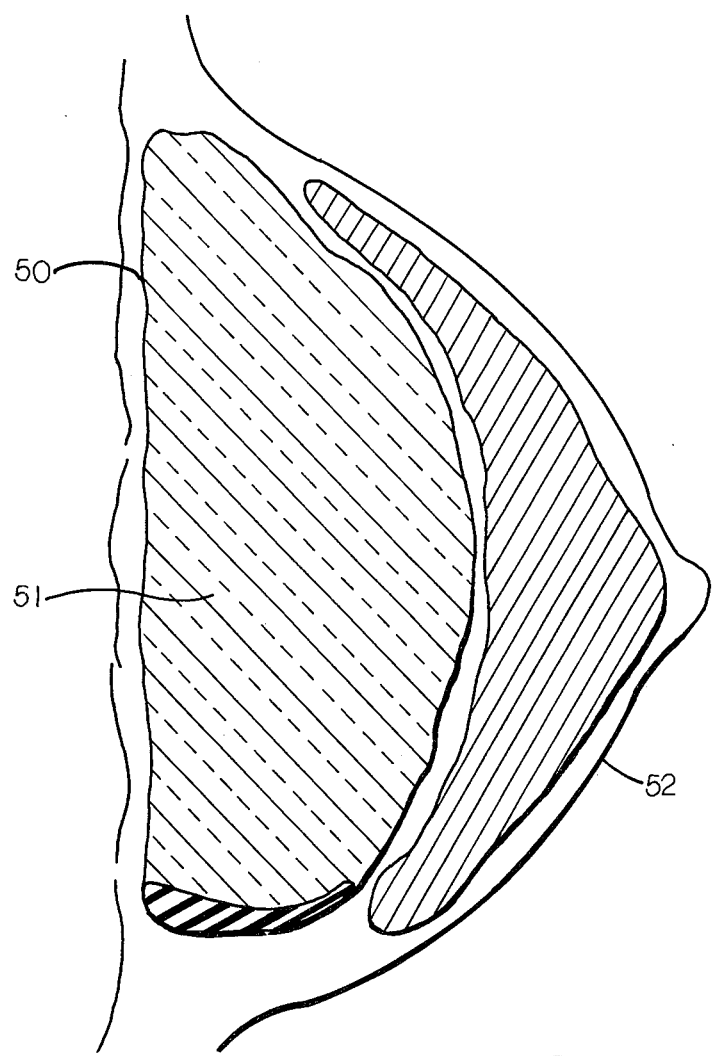
FIG. 5 shows schematically and in cross-section the prosthesis of FIGS. 3 and 4 after the gel filling has swollen.

Referring more specifically to FIG. 5 there is shown prosthesis 50 (which corresponds to prosthesis 40 of FIG. 4). The water injected by needle 45 of FIG. 4 has swollen gel 51 to give breast 52 an altered shape. It can be readily seen from viewing FIGS. 4 and 5 that what has become a relatively large prosthesis has been implanted through a relatively small incision.

EXAMPLES

Example 1

A finitely swellable gel according to the present invention is prepared as follows:

The stopcock hole in a 125 ml. pressure equalizing funnel is plugged with glass wool. The funnel is about half filled with alumina (obtained from Alcoa). The funnel and its contents are placed in an air circulating oven at 200° C. for about 2½ hours and then removed to cool.

After cooling, about 200 ml. n-vinyl-pyrrolidone (VP) is purified by passing it through the activated alumina. The VP is subsequently placed in a stopped bottle which is covered with aluminum foil to reduce exposure to sunlight.

10 ml of the VP is then placed in a 2 oz. (0.0000591 $m^3$) round, wide mouth vial and 20 ml of purified water is then added along with 0.04 g. of Vazo 64 ® (an azo-bis(isobutyronitrile) free radical catalyst to initiate polymerization, available from duPont). This results in a water/vinylic monomer volume ratio of 2.

0.034 ml of vinyltrimethoxysilane (density = 0.968 g/ml.) obtained from Dow Corning Corporation, is added to the solution, providing a vinylic monomer/silane molar ratio of 389.9.

The vial is purged with nitrogen and capped. It is then shaken and allowed to sit for about 10 minutes (until the Vazo 64 ® is almost completely dissolved). The sample is then immersed in a 60° C. constant temperature water bath for 3 hours to achieve polymerization.

The cap is removed from the vial, and the gel is observed to be a stringy, cohesive, response material having good flexural strength and suitable for use in mammary prostheses.

The gel is tested for swell by placing a weighed amount (1.3 g.) in a 2 oz. (0.0000591 $m^3$) round wide mouth vial with an excess (50 ml.) of water for a week. After a week, the excess water is decanted with a paper towel and the polymer is washed with water three times at 10 minute intervals.

The swollen polymer is weighed. After weighing, it is dried in a circulating oven at 50° C. until a constant weight is maintained.

The % swell is calculated according to the following formula:

$$\% \text{ Swell} = \frac{(\text{wt Swollen Polymer}) - (\text{wt Dried Polymer})}{(\text{wt dried polymer})} \times 100$$

The gel of Example 1 has a calculated % swell of 6,200%.

It is seen that the gel of Example 1 has high water swellability and has a stringy, cohesive responsive character.

Examples 2–18

Other gels are formed according to the table below by substantially the same method as detailed in Example 1. Characterization of the gels is shown in Table 2-1.

Table 2-1

| Ex. No. | Vinylic Constituent | Vinylic Comonomer | Mole % Comonomer | HOH/Vinylic Constituent Volume Ratio | Olefinic Silane | Vinylic Constituent/ Silane Mole Ratio | Character of Gel as Prepared | Equilibrium Character of Gel in Large Excess of Water |
|---|---|---|---|---|---|---|---|---|
| 2 | n-vinyl pyrrolidone | | | 1.0 | ViSi(OMe)$_3$ | 194.5 | Very tough, cohesive | 2,100% swell;[c] firm |
| 3 | " | | | 2.0 | " | 48.4 | " | 2,170% swell; firm |
| 4 | " | | | 2.0 | " | 194.5 | " | 3,200% swell; firm |
| 5 | " | | | 3.0 | " | 194.5 | " | 4,450% swell; stringy, cohesive, responsive |
| 6 | " | | | 2.0 | " | 390.0 | " | 6,500% swell; stringy, cohesive, responsive |
| 7 | " | | | 2.0 | ViSi(OEt)$_3$ | 194.5 | " | 3,300% swell; firm |
| 8 | " | | | 3.5 | ViSi(OMe)$_3$ | 149.0 | " | 4,700% swell; stringy, cohesive, responsive |

Table 2-1-continued

| Ex. No. | Vinylic Constituent | Vinylic Comonomer | Mole % Comonomer | HOH/Vinylic Constituent Volume Ratio | Olefinic Silane | Vinylic Constituent/ Silane Mole Ratio | Character of Gel as Prepared | Equilibrium Character of Gel in Large Excess of Water |
|---|---|---|---|---|---|---|---|---|
| 9 | n-vinyl pyrrolidone | | | 5.0 | ViSi(OMe)$_3$ | 98.0 | Very cohesive Penetration Value (PV) 68.5[a] | Slowly soluble |
| 10 | " | | | 6.0 | " | 98.0 | Very cohesive PV 160.0[a] | Slowly soluble |
| 11 | " | | | 7.0 | " | 98.0 | Very cohesive PV 180.0[a] | Soluble |
| 12 | " | | | 8.0 | " | 98.0 | Very cohesive PV 317[a] | Soluble |
| 13 | " | | | 6.0 | " | 196.0 | Very cohesive PV 299[a] | Soluble |
| 14 | " | | | 9.0 | " | 98.0 | Cohesive fluid PV 215[b] | Soluble |
| 15 | " | Hydroxyethyl-methacrylate | 3.5 | 2.0 | " | 392.0 | Very cohesive | Very cohesive, not soluble |
| 16 | n-vinyl pyrrolidone | Hydroxyethyl-methacrylate | 3.9 | 2.0 | ViSi(OMe)$_3$ | 392.0 | Very cohesive | Slightly fragile; not soluble |
| 17 | " | " | 10.0 | 2.0 | None | | Fragile | Fragile; not infinitely soluble |
| 18 | " | " | 10.0 | 5.0 | None | | Fragile | Fragile; not infinitely soluble |

[a]An aluminum penetration rod 6 inches (15.24 cm) long and ⅛ inch (0.32 cm.) in diameter having a flat, round, ¼ inch (0.64 cm) diameter brass pressure foot is suspended over a sample of gel contained in a round, wide-mouth jar. The mouth of the jar is sufficiently wide to allow ½ inch (1.27 cm) clearance. The jar is about 1 inch (2.54 cm) deeper than the expected penetration distance of the foot. The combined weight of the rod and foot is 19.5 g. The rod is released and allowed to penetrate the gel for five seconds. The Penetration Value (PV) is the distance which the rod penetrates the gel in tenths of a millimeter.
[b]As in [a] except using a 1 inch (2.54 cm) aluminum pressure foot and a combined weight of 14.5 g.
[c]Precise repeatability of % swell base data is increasingly difficult as higher swellabilities are achieved. Values shown are averages from several procedures.

It is seen from Examples 2-16 that a variety of useful, hydrophilic gels according to the present invention are possible. Further, it is seen from Examples 15 and 16 that useful terpolymers are possible, but the character of the gels can be adversely affected by adding more than minor amounts of a comonomer. This is true even if a crosslinking comonomer is omitted as in comparative Examples 17 and 18.

Example 19

Six adult mice (3 males and 3 female) are each given a single intraperitoneal injection of the gel of Example 10. In each case, the amount of gel is adjusted so that it equals 25 ml/kg. of body weight. The gel is of sufficient volume to make a readily visible bulge beneath the skin in each mouse.

The animals are returned to their cages and observed for 21 days. In each case, the bulge slowly dissipates within 12 days with no observable systemic toxicity.

It is seen from Example 19 that an infinitely soluble hydrophilic gel of the present invention is absorbed by the body without adverse effect.

The present invention has been disclosed in the above teachings, drawings and examples with sufficient clarity and conciseness to enable one skilled in the art to make and use the invention, to know the best mode for carrying out the invention and to distinguish it from other inventions and from what is old. Many variations and obvious adaptations of the invention will readily come to mind, and these are intended to be contained within the scope of the invention as claimed below.

That which is claimed is:

1. A water swellable hydrophilic gel comprising a crosslinked copolymer of a water soluble vinylic constituent in aqueous solution and an olefinic hydrolyzable silane having the formula $X_mR_nSi(OR')_{4-(n+m)}$ wherein X is an unsaturated group, m is at least 1 and R' and R are organic radicals, n being 0 to 2, wherein the volume ratio of water to vinylic constituent is from about 0.5 to about 10 while the mole ratio of vinylic constituent to hydrolyzable silane is from about 50 to about 600, wherein copolymerization is via the unsaturated groups and wherein crosslinking is by condensation reactions.

2. The gel of claim 1 wherein the volume ratio of water to vinylic constituent and the mole ratio of vinylic constituent to hydrolyzable silane are selected to produce a gel which is water swellable to an infinite extent.

3. The gel of claim 1 wherein the volume ratio of water to vinylic constituent and the mole ratio of vinylic constituent to hydrolyzable silane is selected to produce a gel which is water swellable to a finite extent.

4. The gel of claim 1 wherein the volume ratio of water to vinylic constituent and the mole ratio of vinylic constituent to hydrolyzable silane is selected to produce a slowly soluble gel.

5. The gel of claim 1 wherein the vinylic constituent is selected from the group consisting of n-vinylpyrrolidone and copolymers and terpolymers of n-vinylpyrrolidone with minor amounts of comonomers selected from the group consisting of 2,4-pentadiene-1-ol; acrylamide derivatives of the formula

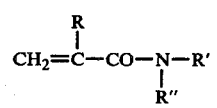

wherein R is —H or CH$_3$ and R' and R" are H, —CH$_3$, —C$_2$H$_5$ or —CH$_2$CHOHCH$_3$; and hydroxylalkylmethacrylates of the formula

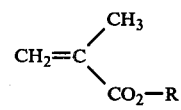

wherein R is —CH$_2$CH$_2$OH; and wherein the olefinic hydrolyzable silane is selected from the group consisting of vinyltrimethoxy-silane, vinyltriethoxysilane, ethylvinyldimethoxysilane, allyltrimethoxysilane and 3-trimethoxysilylpropylmethacrylate.

6. A surgically implantable mammary prosthesis which comprises:
   (a) a flexible container made of surgically implantable material having an outer surface shaped to approximate the general form of the human breast; and
   (b) a filling within the container of the gel of claim 1.

7. The prosthesis of claim 6 wherein the filling within the container comprises the gel of claims 2, 3 or 4.

8. The prosthesis of claim 6 wherein the filling within the container comprises an amount of the gel of claim 3 insufficient to support the prosthesis and wherein the container is adapted to supply the gel with an amount of aqueous fluid after the prosthesis has been implanted, the amount of aqueous fluid being sufficient to swell the gel so that the prosthesis is supported.

9. The prosthesis of claim 8 wherein the container includes a silicone gel valve for supplying a sterile aqueous fluid to the gel.

UNITED STATES PATENT AND TRADEMARK OFFICE
CERTIFICATE OF CORRECTION

PATENT NO. : 4,138,382
DATED : February 6, 1979
INVENTOR(S) : KEITH E. POLMANTEER It is certified that error appears in the above-identified patent and that said Letters Patent are hereby corrected as shown below:

Column 2, line 24, "to" should read --so--

Column 3, line 33, "then" should read --the--

Column 3, line 68, "$X_m R_n Si(OR')_{4-(n-m)}$" should read --$X_m R_n Si(OR')_{4-(n+m)}$--

Column 6, line 23, "response" should read --responsive--

Column 8, Formula that starts on line 55, "$CH_2=\overset{R}{\underset{|}{C}}-CO-N-\underset{|}{R'}$"
                                                                    $R''$ should read --$CH_2=\overset{R}{\underset{|}{C}}-CO-N-\underset{|}{R'}$--
                                                        $R''$

Signed and Sealed this

Second Day of October 1979

[SEAL]

Attest:

RUTH C. MASON
Attesting Officer

LUTRELLE F. PARKER
Acting Commissioner of Patents and Trademarks